US012251275B1

(12) United States Patent
Salmassy

(10) Patent No.: US 12,251,275 B1
(45) Date of Patent: Mar. 18, 2025

(54) METHOD AND SYSTEM FOR PROVISIONING OF DENTAL IMPLANTS AND RELATED SERVICES

(71) Applicant: Alliance Capital Management, Auburn, CA (US)

(72) Inventor: David A. Salmassy, Auburn, CA (US)

(73) Assignee: ALLIANCE CAPITAL MANAGEMENT, Auburn, CA (US)

(*) Notice: Subject to any disclaimer, the term of this patent is extended or adjusted under 35 U.S.C. 154(b) by 0 days.

(21) Appl. No.: 18/092,003

(22) Filed: Dec. 30, 2022

Related U.S. Application Data

(60) Continuation of application No. 15/297,368, filed on Oct. 19, 2016, now Pat. No. 11,583,371, which is a
(Continued)

(51) Int. Cl.
*A61C 13/00* (2006.01)
*A61B 6/03* (2006.01)
*A61B 6/51* (2024.01)
*A61C 1/08* (2006.01)
*A61C 8/00* (2006.01)
*A61C 13/107* (2006.01)
(Continued)

(52) U.S. Cl.
CPC .......... *A61C 13/0004* (2013.01); *A61B 6/032* (2013.01); *A61B 6/51* (2024.01); *A61C 1/084* (2013.01); *A61C 8/0089* (2013.01); *A61C 13/0001* (2013.01); *A61C 13/34* (2013.01); *G16H 20/30* (2018.01)

(58) Field of Classification Search
CPC ............ A61C 13/0004; A61C 13/0001; A61C 13/340006; A61C 1/084; A61C 1/082; A61C 8/0089; G16H 20/30; G16H 20/00; A61B 6/032; A61B 6/14; A61B 6/03; A61B 6/02
USPC ......................................... 433/213
See application file for complete search history.

(56) References Cited

U.S. PATENT DOCUMENTS

| 5,320,529 | A | * | 6/1994 | Pompa | A61C 3/02 |
| | | | | | 433/76 |
| 11,583,371 | B1 | * | 2/2023 | Salmassy | A61C 8/00 |
| 2008/0085489 | A1 | * | 4/2008 | Schmitt | A61C 1/084 |
| | | | | | 433/75 |

OTHER PUBLICATIONS

Marchack An immediately loaded CAD/CAM-guided definitive prosthesis: A clinical report, The Journal of Prosthetic Dentitstry, vol. 93 No. 1, Feb. 2005, pp. 8-12—document from U.S. Appl. No. 13/078,637. (Year: 2005).*

(Continued)

*Primary Examiner* — Ralph A Lewis
*Assistant Examiner* — Mirayda A Aponte
(74) *Attorney, Agent, or Firm* — Husch Blackwell LLP; Bryan D. Stewart

(57) ABSTRACT

The present invention relates to a system and method for dental implant and restorative services. By locating the key functions at one physical location, dental implant services are efficiently provided to patients. These functions include a treatment coordinator, a direct marketer, a restorative doctor/prosthodontist, a surgeon, an imaging area, and a dental laboratory, Further, services for dentate patients are improved by utilizing advanced dental implant methods and systems. These methods and systems include both model-based services and CT (computed tomography) guided surgery services. Using these services, improved surgical guides for dental implants are constructed.

16 Claims, 4 Drawing Sheets

Related U.S. Application Data continuation of application No. 13/078,637, filed on Apr. 1, 2011, now Pat. No. 9,508,106, which is a division of application No. 12/005,909, filed on Dec. 28, 2007, now abandoned.

(60) Provisional application No. 60/877,940, filed on Dec. 29, 2006.

(51) Int. Cl.
*A61C 13/34* (2006.01)
*G16H 20/30* (2018.01)

(56) References Cited

OTHER PUBLICATIONS

De Moyer, Method for Producing a Dental Prosthesis and a Device for Carrying out Said Method, machine translation, (Year: 2006).*

* cited by examiner

METHOD AND SYSTEM FOR PROVISIONING OF DENTAL IMPLANTS AND RELATED SERVICES

CROSS REFERENCE

The present application is a continuation of U.S. patent application Ser. No. 15/297,368, filed Oct. 19, 2016, which is in turn, is a continuation of U.S. patent application Ser. No. 13/078,637, filed Apr. 1, 2011, which is in turn, is a divisional of U.S. patent application Ser. No. 12/005,909, filed Dec. 28, 2007, which claims priority from U.S. Provisional Application No. 60/877,940 filed Dec. 29, 2006. Each of the foregoing patent applications are hereby incorporated by reference in their entirety.

FIELD OF THE INVENTION

This invention relates to dental implant surgery and restoration, and more particularly improved methods and systems for providing dental implant services and improved techniques for providing dental implant services to dentate patients. This invention also generally relates to the provisioning of other health care services.

BACKGROUND

As we age, some of us will lose teeth due to disease, injury, or simple daily wear. In addition to bringing about unwanted changes to a person's facial appearance, missing teeth have a negative effect on that person's confidence and self-esteem. With the advent of implant dentistry, however, those who are missing one, two or several teeth no longer have to accept a lifetime of embarrassment and inconvenience. Dental implants, sturdy titanium posts that are anchored directly into the jawbone and topped with realistic replacement teeth, provide the security and usability of permanently placed teeth.

Dental implants are a restorative dentistry option that allows patients to replace missing teeth with ones that look, feel, and perform like their own. During the first step of this procedure, a doctor skilled in implant dentistry surgically places a titanium screw or post in the patient's jaw. After the gums have healed around the embedded post, a replacement tooth is attached to the top of it.

Dental implants are a substantial improvement over conventional dentures.

They're more stable and user-friendly than many other teeth replacement options, and because the posts that secure dental implants in place are integrated into the jaw, they also help prevent bone loss and gum recession (because the pressure of chewing on the implant's crown stimulates the underlying bone and prevents it from deteriorating from disuse). However, some medical circumstances—including radiation therapy in the mouth area, and diseases such as diabetes lower the success rate for implant dentistry. For that reason, patients must undergo a rigorous screening process before they may proceed with implant dentistry.

Patients can choose from a variety of options to replace missing teeth. In addition to dental implants, there are removable partial dentures held in place by wire clips; fixed dental bridges cemented into position by crowns placed on the teeth adjacent to an empty space; and traditional full dentures.

The concept behind dental implant surgery was developed by a Swedish orthopedic surgeon and researcher, Per Ingvar Brinemark, who found that a titanium implant could naturally bond with bone material. Termed "osseointegration," this phenomenon ushered in what is now considered the most ideal method of permanently replacing missing teeth.

The surgical procedure used to insert dental implants may be performed under local anesthetic. The implant dentist begins by making an incision in the gums, exposing the bone in the jaw, and making the holes to accommodate dental implant placement. The dental implants are then secured in the jawbone, and the gums are closed with stitches.

Implant dentistry is a comprehensive tooth replacement process rather than a quick fix. Once a dental implant has been placed during oral surgery, the bone is given time to grow and fuse around the implant base. At the time of implant placement surgery, the objective is to achieve primary stability of the implant fixture prior to considering immediate provisionalization or restoration. For dental implants in the upper jaw, the osseointegration period will take approximately six months. For those in the lower jaw, it will take approximately three months.

When the bone has successfully grown around the dental implant following oral surgery, a dentist will add an artificial tooth to the post. This process varies depending on the types of dental implants used. After the posts are topped with prosthetic teeth, any necessary dental bridges or full/partial dentures can also be inserted into the configuration.

Factoring in the time it requires for the gums to heal around the posts after dental implant placement, traditional dental implant surgery generally requires from five months to two years to complete. However, a new version of the procedure enables some patients to literally have "Teeth in a Day (or Hour)." This innovative dental implant restoration protocol allows patients to get their new teeth all at once, dramatically reducing treatment time and immediately restoring the mouth to full function. However, "Teeth in a Day (or Hour)" does not include the initial appointments and necessary preparation for the implant surgery.

This innovative dental implant restoration protocol is based upon the developments of immediate loading of Brinemark Implants. The concept of immediate function on endosseous implants has historic precedents in dentistry. The biologic and mechanical results of treatment using endosseous implants such as blades and tripodial pins, led to their demise and a moratorium on such treatment over three decades ago. In the early 1980's the process of osseointegration was introduced to North America following a stringent protocol developed by the Swedish physician and researcher, Per Ingvar Brinemark. This protocol required the undisturbed and unloaded healing of bone around the implants for a specified period of time prior to prosthetic application. Recently, however, a small number of clinical researchers have modified Brinemark's original protocol to begin loading Brinemark implants early or even immediately in specific areas. Success rates have varied depending upon the quality and quantity of bone; however, the concept has proven to be effective for certain individuals.

The cost of dental implants varies depending on the number of missing teeth and the area of the country in which the implant dentistry is performed. The cost of dental implants ranges from $2,000 to $4,000. Hence, it is desirable for science and technology to continue to develop to minimize the cost to patients.

Fortunately, financing is available for people who require advanced treatment such as dental implant placement. Third party financing companies can provide credit and many dental offices offer installment plans for their dental implant patients to help manage the cost of replacing missing teeth.

Overall, the technology of dental implants has significantly improved the options and quality for dental implant services. Such technologies as guided surgery based on three dimensional CT (computed tomography) imaging and model-based guides have given the industry significant options for patient care. However, to provide these services requires the coordination for several functional specialties, including medical restoration, oral surgery, computer imaging, and dental manufacturing laboratories.

More specifically, there are several professional functions and services necessary to provide dental implants to patients. These functions and services include treatment coordinator, financial services, direct marketing, restorative doctor or prosthodontists, oral surgeon, imaging services, and dental implant laboratory. In the prior art, several or all of these functions and services are not co-located. Accordingly, despite the advancements in technology offering such hype as "teeth in a day", this reality can not be achieved under the prior art conditions. The lack of an efficient physical arrangements results in significant delays in providing service and additional costs. The present invention addresses these issues.

SUMMARY

The present invention provides for the complete co-location of all necessary functions and services for modern dental implant services. Co-location means one physical facility for treatment coordinator, financial services, direct marketing, restorative doctor/prosthodontist, surgeon, imaging area, and dental laboratory. Such an arrangement allows for expedient and successful dental implant services at lower costs.

Additionally, this efficient arrangement is ideal to support recent advances in dental implants. Such advances as model-based planning for guided implant surgery and CT Guide services for dentate patients are efficiently implemented with the present invention.

The benefit of co-location of all essential services can also be beneficial for other types of health care services. Besides providing timely and quality medical service and cost, such arrangements provide one point of customer contact.

The technology of model-based planning for guided implant surgery provides patients with a method to replace one to three teeth, or more, with implants. The cost for this procedure is reduced because the expense of the traditional CT-guided surgery is eliminated, while the quality of the procedure is maintained given the accuracy of the guided models.

Another recent advance in dental implants is CT Guide services for dentate patients (i.e., patients who do have a significant number of teeth). The use of computed tomography (CT) technology for placement of dental implant placement and has allowed the surgical and restorative team to idealize and optimize dental implants placement and subsequent restorative prosthetic design.

DETAILED DESCRIPTION

The article, "Guided Implant Surgery: Part I Model-Based Planning with NobelGuide™", David A. Salmassy, D.M.D, The Seattle Study Club Journal, Vol. 10 Spring, No. 3 2006, is incorporated by reference.

The article, "CT-Guided Immediate Implant Placement with Full Arch Provisionalization in a Partially Dentate Patient", David A. Salmassy, D.M.D, The Seattle Study Club Journal, Vol. 2, No. 1; Fall 2007, Pg 22-27, is incorporated by reference The present invention provides for improved services for dental implants, as well as other health services. Improved services are defined in terms of the success of the services, the time efficiency and the cost of the services.

Figure 1:
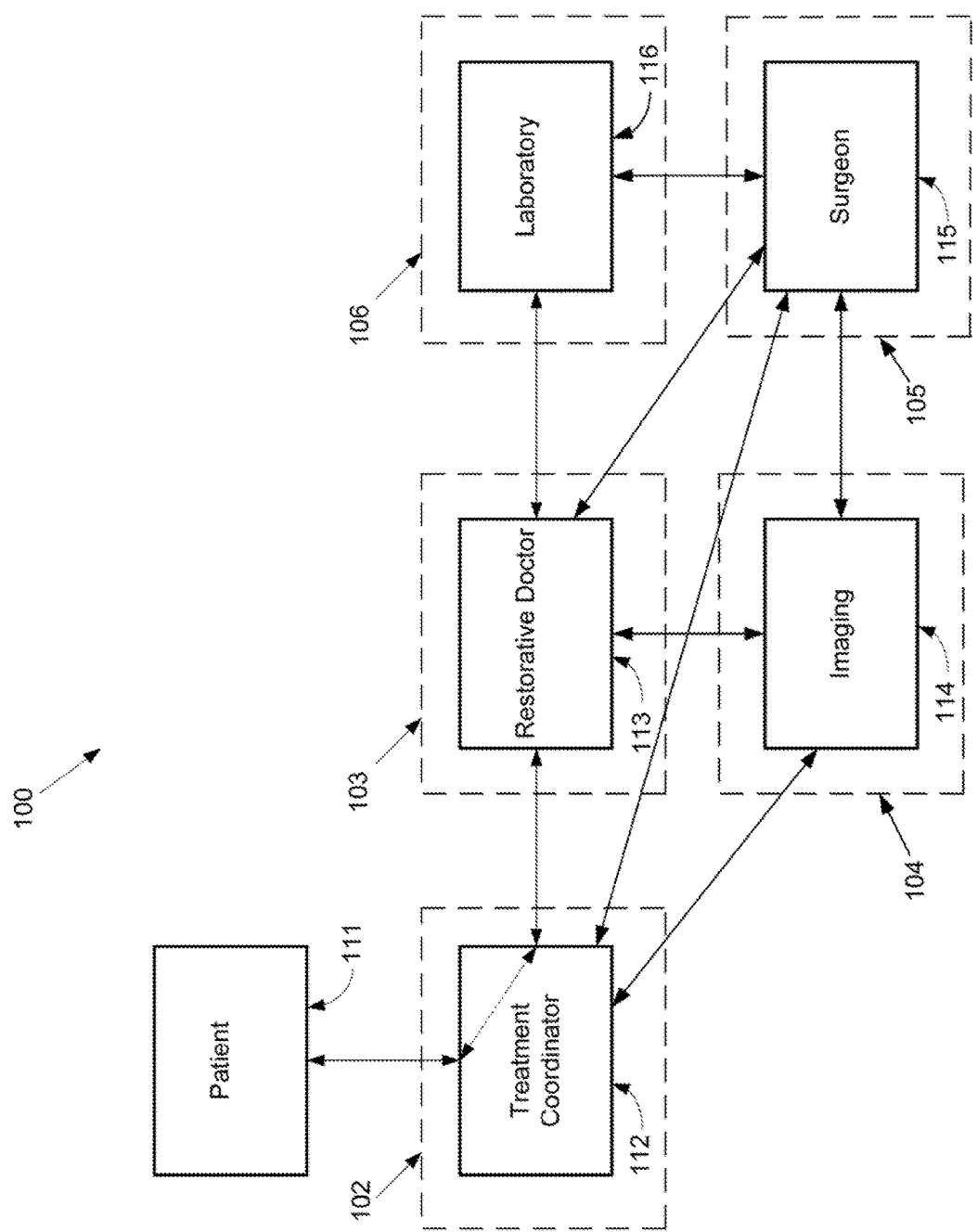
FIG. 1 depicts the relationships between the professional functions and services and the patient according to the prior art.

The prior art method 100 is depicted in FIG. 1. In this case the Patient 111 contacts the Treatment Coordinator 112 at location 102 for dental implant services. This contact may occur because of a reference from a medical or dental professional, due to a priori knowledge, or due to random selection. In any case, it is not a controlled or efficient process.

The Treatment Coordinator 112 will discuss with Patient 111 their dental situation and their financial/insurance situation relative to payment of dental services. The Treatment Coordinate 112 will schedule an appointment with the Restorative Doctor 113 at location 103.

The Restorative Doctor 113 is a dentist with special training in planning and making replacements for missing teeth or other structures of the oral cavity to restore the patient's appearance, comfort, and/or health. As a trained dentist, the Restorative Doctor 113 is able to handle most of the dental implant needs of the Patient 111. However, for more complex issues, including full mouth restorations, a Prosthodontist may be required. A Prosthodontist is a restorative doctor with a significant higher level of training than the Restorative Doctor 113. In some cases the Prosthodontist is a consultant to the Restorative Doctor 113 and the Surgeon 115.

The Restorative Doctor 113 will examine Patient 111, and advise them of their restorative options. With patient acceptance of this diagnosis, the Restorative Doctor will order imaging pictures to be taken at Imaging 114. The Patient 111 will travel to Imaging 114, located at 104 and have imaging pictures taken of the dental area in need of restoration. The Restorative Doctor 113 will receive the imaging results and have them sent to the Surgeon 115 at location 105. After a review of the imaging results, the Restorative Doctor 113 and the Surgeon 115 will consult and recommend a plan for the restoration. The Restorative Doctor 113 via the Treatment Coordinator 112 will communicate this plan to Patient 111 for their concurrence and approval.

After Patient 111 approval of the plan, the Restorative Doctor 113 will design and order the dental implant apparatus from the dental Laboratory 116 at location 106. Depending upon the patient situation, the dental Laboratory 116 may need to consult the Surgeon 115 to finalize the dental implant apparatus.

Depending upon the patient situation, the Surgeon 115 may need to restore (build up) the patient's bone volume to allow for successful placement of the implant. This process may take several months.

Via the Treatment Coordinator 112, the Patient 111 schedules an appointment with the Surgeon 115 for the installation of the restorative dental implants. This procedure will be preformed at the surgeon's facility at location 105. Following surgery the Patient 111 returns to Imaging 114 at location 104 to have imaging services performed on the surgery results. The Surgeon 115 reviews and approves the results and provides the same information to the Treatment Coordinator 112 and to the Restorative Doctor 113.

If the aforementioned processes have been well planned, the dental implant process can be completed and the restoration process can begin in the same day. Hence the term, "teeth in day", or "teeth in an hour" have been coined to define the expediency of the dental implant technology. However these terms do not include the time required for the planning and preparation processes as described in the above paragraphs. Nor do these terms include the entire restoration process. The time required these processes will be measured in weeks or months.

Figure 2:
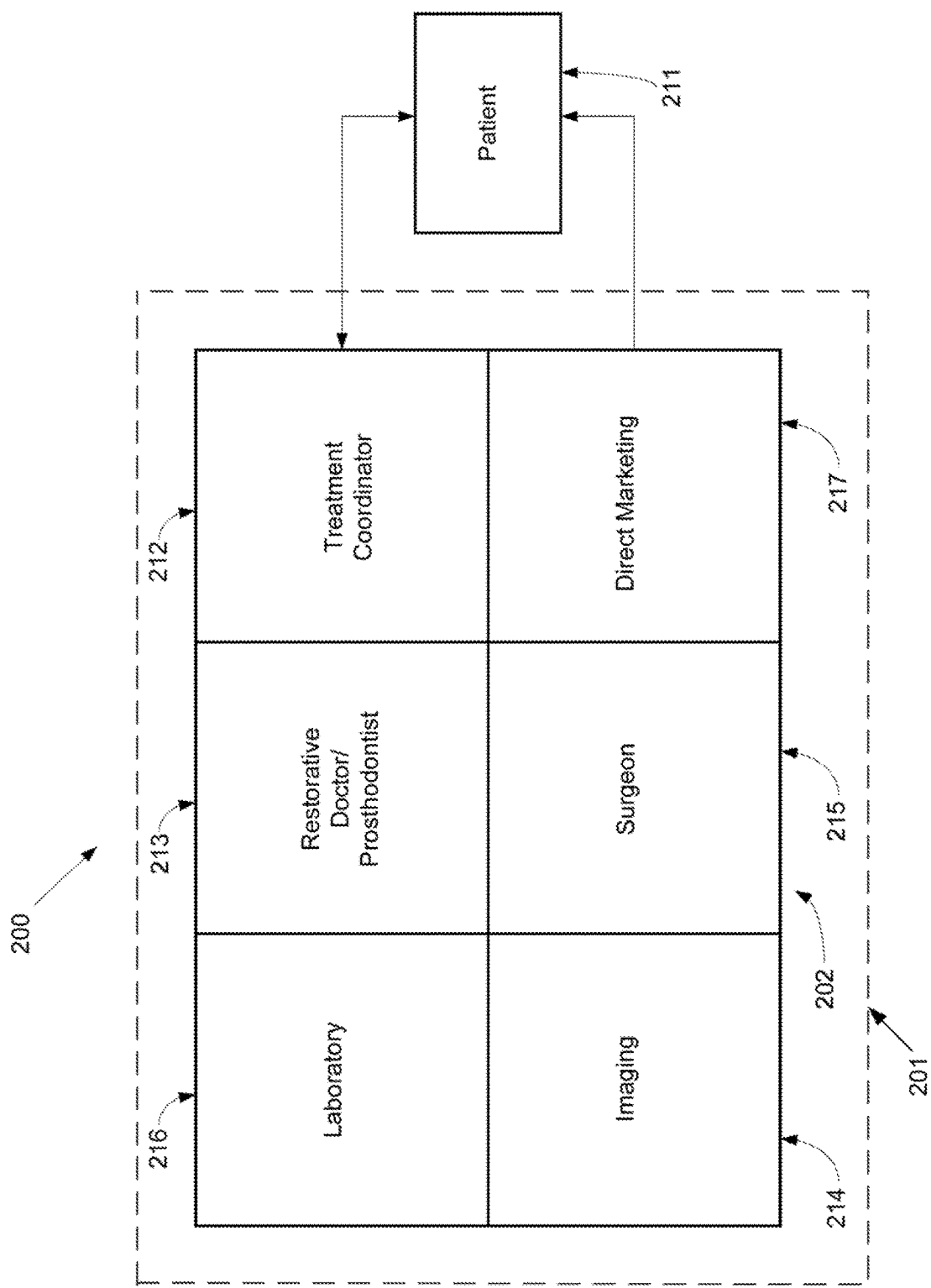
FIG. 2 depicts the relationships between the professional functions and services and the patient according to one embodiment of the present invention.
Figure 3A:
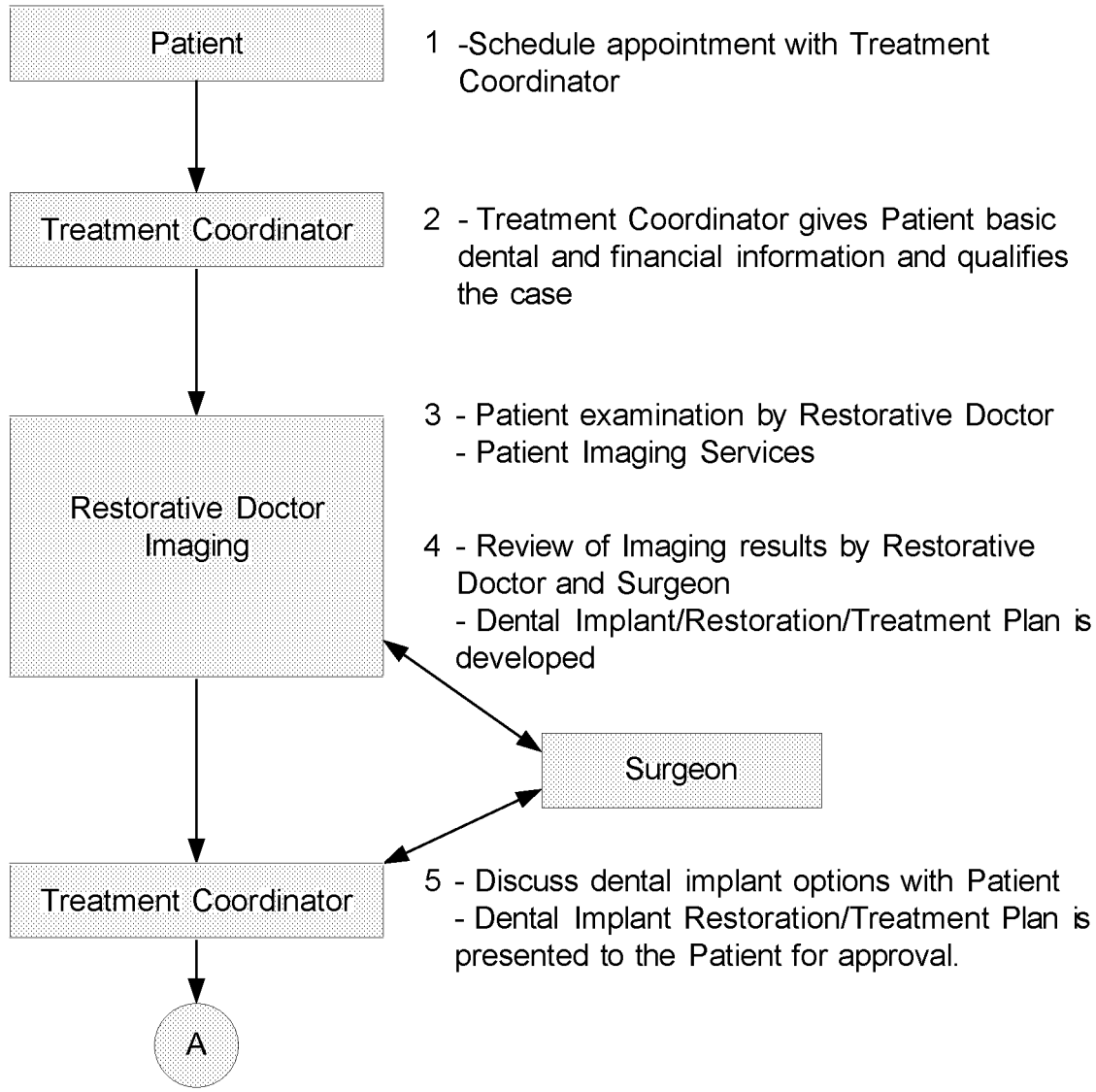
FIG. 3A depicts steps for the the flow of activities for a dental implant procedure, according to one embodiment of the present invention.
Figure 3B:
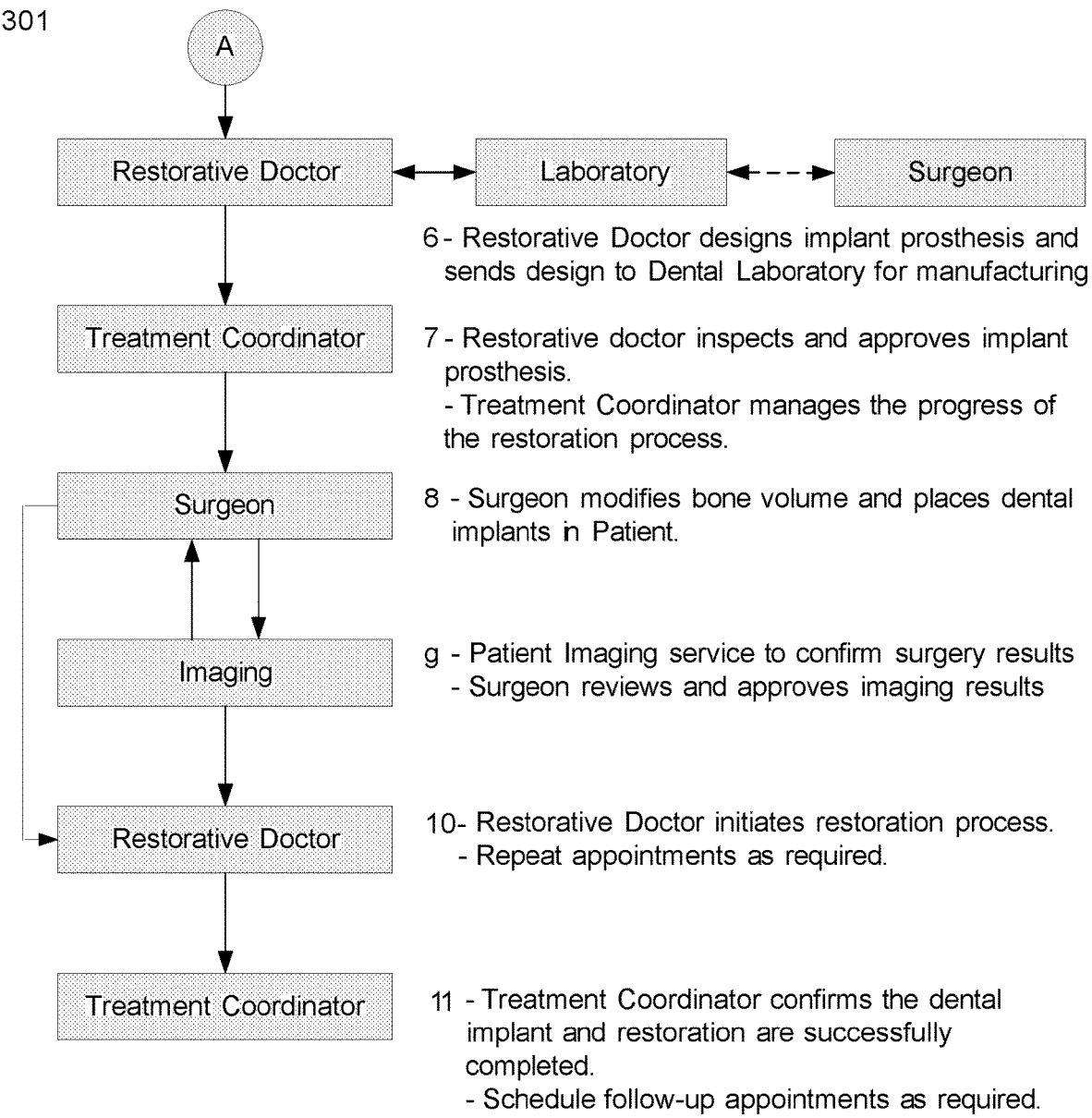
FIG. 3B depicts additional steps for the flow of activities for a dental implant procedure, according to one embodiment of the present invention.

The present invention 200 is depicted on FIG. 2. In FIGS. 3A, 3B the flow of activities for the present invention is illustrated, according to one embodiment 300/301. The efficiency and cost of this dental implant procedure is impacted by the logistics of the professional functions and services involved with the flow. All of the boxes on the left hand side of FIGS. 3A, 3B require participation by the patient.

The flow of activities for embodiment 300/301 comprise the following steps:

Step 1—Schedule appointment with Treatment Coordinator.

Step 2—Treatment Coordinator gives Patient basic dental and financial information and qualifies the case.

Step 3—Patient examination by Restorative Doctor-Patient Imaging Services. As illustrated in FIGS. 3A, 3B, the patient examination and patent imaging may occur in any order.

Step 4—Review of Imaging results by Restorative Doctor and Surgeon—Dental Implant/Restoration/Treatment Plan is developed.

Step 5—Discuss dental implant options with Patient—Dental Implant Restoration/Treatment Plan is presented to the Patient for approval.

Step 6—Restorative Doctor designs implant prosthesis and sends design to Dental Laboratory for manufacturing—Surgeon monitor Laboratory activity as needed. Restorative doctor inspects and approves implant prosthesis.

Step 7—Treatment Coordinator manages/coordinates the progress of the restoration process including the progression through patient imaging and development of restorative prosthesis of patient as needed.

Step 8—Surgeon extracts teeth and modifies bone volume and places dental implants in Patient.

Step 9—Patient Imaging service to confirm surgery results—Surgeon reviews and approves imaging results Step 10—Restorative Doctor initiates restoration process.—Repeat appointments as required.

Step 11—Treatment Coordinator confirms the dental implant and restoration are successfully completed.—Schedule follow-up appointments as required.

Per FIG. 2, all of the necessary functions for a dental implantation are co-located at location 201 at a single facility 202. The functions in this facility 202 include the Treatment Coordinator 212, Restorative Doctor 213 (and/or Prosthodontist), in-house Laboratory 216, Imaging 214, and Surgeon 215. In addition, a function of Direct Marketing 217 is a part of the present invention, and may be co-located.

In as much as these functions are co-located, any of the functions can directly and efficiently communicate with any other function in facility 202. Hence, the Treatment Coordinator 212 can directly communicate with the Restorative Doctor 213, the in-house Laboratory 216, Imaging 214, the Surgeon 215, and Direct Marketing 217. Similar communication relationships exist for any of the other functions, in a similar manner as described.

Direct Marketing 217 provides a "direct" marketing communication link between the dental implant center and potential customers. Via Direct Marketing 217, the benefits of the dental implant center are efficiently communicated. The benefits include the quality, reliability, timeliness and cost effectiveness of the services.

With the present invention 200, the Patient 211 will initially communicate with the Treatment Coordinator 212. The Treatment Coordinator 212 will discuss with Patient 211 their dental situation and their financial/insurance situation, relative to payment of dental services. The Treatment Coordinate 212 will schedule an appointment with the Restorative Doctor 213 at location 201.

The Restorative Doctor 213 (and/or Prosthodontist) is a dentist with special training in planning and making replacements for missing teeth or other structures of the oral cavity to restore the patient's appearance, comfort, and/or health. As a trained dentist, the Restorative Doctor 213 is able to handle most of the dental implant needs of the Patient 211. A Prosthodontist is a restorative doctor with an advanced level of training in the implant restoration process.

The Restorative Doctor 213 will examine Patient 211, and advise them of their restoration options. With patient acceptance of this diagnosis, the Restorative Doctor 213 will immediately order images to be taken at Imaging 214, located in the facility 202. The Patient 211 will walk to Imaging 214 and have images taken of the dental area in need of restoration. In a few minutes, the Restorative Doctor 213 will receive the imaging results and have them sent to (or available for) the Surgeon 215. After a review of the imaging results, the Restorative Doctor 213 and the Surgeon 215 will consult and recommend a treatment plan for the restoration. The Restorative Doctor 213, the Treatment Coordinator 212 and the Surgeon 215 will communicate this plan to Patient 211 for their concurrence and approval. These described actions can occur during the same appointment on the same day.

The Patient 211 will be more likely to accept the treatment plan since the complete dental implant and restoration information is presented in a timely manner and can be immediately discussed with all of the key practitioners involved with these services, including the Treatment Coordinator 212, Restorative Doctor 213, and the Surgeon 215.

After Patient 211 approval of the plan, the Restorative Doctor 213 will design and order the dental implant apparatus from the dental Laboratory 216 at location 201. Depending upon the patient situation, the in-house dental Laboratory 216 may need to consult the Surgeon 215 to finalize the dental implant apparatus. Given that the medical professionals and the dental laboratory are co-located, this process will be completed in a more timely manner that the prior art 100 of FIG. 1. Typically the present invention process will be completed in days, rather than weeks with the prior art process.

Depending upon the patient situation, the Surgeon 215 may need to restore (build up) the patient's bone volume to allow for successful placement of the dental implants. This process may take several months.

Via the Treatment Coordinator 212, the Patient 211 schedules an appointment with the Surgeon 215 for the installation of the dental implants. If the aforementioned processes have been well planned, the dental implant process can occur in a day. Following surgery the Patient 211 walks to Imaging 214 at the facility 202 to have imaging services performed on the surgery results. The Surgeon 215 reviews and approves the results and provides the same information to the Treatment Coordinator 212 and to the Restorative Doctor 213.

During the same day, the Restorative Doctor 213 can place the restoration on the implants and thus begin the restorative process.

In summary, the present invention as depicted in FIG. 2 provides quality, timely, and cost effective treatment for dental implant services, as compared with the prior art method depicted in FIG. 1. Further, as technology continues to improve, the present invention will facilitate the success and efficiency of advanced dental implant methods, such as the ones described below.

The following is a description of the method of providing dental implant and restorative services.

A method of providing dental implant and restorative services to a patient comprises utilizing one physical location for the services, and providing to the patient, the services related to a treatment coordinator, a restorative doctor/prosthodontist, a surgeon, an imaging area, and a dental laboratory. The services of the method further comprise providing to the patient, the services related to a direct marketer.

The services of the method further comprises the patient, making an appointment with the treatment coordinator; the treatment coordinator providing the patient, dental and financial information, providing the patient, qualification information concerning patient's case, managing all patient activities, while the patient is receiving the services.

From the imaging area, imaging services are provided in order to characterize the patient's case, and the results of the imaging services are sent to the restorative doctor/prosthodontist and the surgeon. The restorative doctor/prosthodontist and the surgeon and examine the patient, and review the results of the imaging services.

Additionally, the restorative doctor/prosthodontist and the surgeon, discuss options for a dental implant and restoration plan, agree on the dental implant and restoration plan, and communicate the dental implant and restoration plan to the treatment coordinator.

The treatment coordinator, at the patient's appointment, communicates the dental implant and restoration plan to the patient. The patient provides approval for the dental implant and restoration plan.

The restorative doctor/prosthodontist design dental implant prosthesis per requirements of the dental implant and restoration plan, send the dental implant prosthesis design to the dental laboratory for manufacturing of the dental implant prosthesis, receives the dental implant prosthesis from the dental laboratory, and inspects the dental implant prosthesis relative to requirements of the dental implant and restoration plan.

The surgeon provide services for extraction of teeth and modification of bone volumes for the patient per the dental implant and restoration plan, provides surgical placement of the dental implant prosthesis into the patient, obtains image results of the surgical placement from the imaging area, reviews and approves the image results of the surgical placement discusses with the patient the dental implant results, comprising the results of the surgical placement and of the imaging, and notifies the restorative doctor/prosthodontist and the treatment coordinator of completion of the dental implant surgical placement. The restorative doctor/prosthodontist provides the restoration services.

The treatment coordinator reviews the dental implant and restoration services results with the patient, schedules further appointments with the restorative doctor/prosthodontist, and confirms the dental implant and restoration services are completed.

Guided Implant Surgery: Model-Based Planning

To improve the success rate of dental implants, there have been a number of advancements in the technology. One of the most recent advances in dental implants include model-based planning with CT guided dental implant surgical treatment planning software. This application is described in "Guided Implant Surgery: Part I Model-Based Planning with NobelGuide™, by David A. Salmassy, D.M.D, published in the Seattle Study Club Journal Vol. 10 Spring, No. 3 2006. The contents of this publication are incorporated by reference in this application.

Introduction

The use of surgical guides in implant dentistry is not a new concept, but rather the standard of care in many circles. For years, dental laboratories have been providing the implant surgeon with guides designed to deliver the ideal implant position and axial inclination for both single-unit and multiple implant cases. Now a new technology has been developed to enable surgical and restorative doctors to precisely control the insertion of the implant fixture. Combined with the advanced treatment protocols for flapless surgery, extraction and immediate placement, and immediate loading with provisionalization, the new surgical-guide technology has taken the implant team well outside of the original box outlined by Branemark in 1983. The treatment timeline has been dramatically decreased, greatly benefiting both practitioners and patients alike. Guided surgery with advanced surgical templates has taken implant surgery to the next level by allowing for control over the depth and angulations of fixture placement. These guides have been borne out of advanced three-dimensional imaging and modeling (CT-guided surgery), as well as the basic approach of transferring clinical and radiographic data to a working model of the proposed surgical site (model-based surgery). The application of standardized principles allows the clinician to construct a highly accurate surgical template to reproduce the desired fixture location at the time of placement. Guided surgery is a collaborative effort driven by the restorative needs of a particular case as supported by the biologic availability of the anatomic components. CT-guided surgical template fabrication can be an excellent option for appropriate cases, such as an edentulous maxilla, or mandible and the multiunit continuous restoration. For other cases, model-based surgery has the advantage of the use of traditional imaging and clinical information every practitioner has become familiar with. It is the transfer of the information from the patient to the model and the construction of the surgical template that makes this technique appealing and practical at the same time.

Whereas the concept of immediate loading for dental implants has been extensively reported on, the application of immediate implant-placement torque values has recently received significant attention. The concept of primary implant stability is crucial to successful provisionalization. It has been suggested that minimum insertion-torque values of 35-45 Ncm be achieved prior to placement of either the provisional or definitive restoration at the time of surgery. In the case of immediate extraction and implant insertion, primary stability of the implant fixture is as important as the stability of the provisional restoration and its influence of contour on the surrounding soft tissues. Immediate implant insertion has been credited with preservation of the papillary architecture. The purpose of this article is to discuss the design and application of model-based surgery for implant fixture placement in simple and advanced treatment protocol applications.

Technique

The approach involves correlating the clinical and radiographic information and transferring it to the working models of the patient. At the initial implant consultation, the practitioner should acquire a baseline level of information and imaging including periapical imaging, panoramic imaging standardized using the Frankfurt horizontal plane, and a photographic image of the proposed surgical site. Periodontal evaluation should include the tissue biotype, as well as interproximal, lingual/palatal, and facial probing depths. Diagnostic models and bite registration will assist in reproducing the clinical situation prior to treatment. If the site is edentulous, the imaging and models will allow for the determination of the hard- and soft-tissue volume and whether the site is compatible with an accelerated treatment protocol. The same is true for dentate sites where interproximal bone height and width, soft-tissue topography, and interdental contact point levels are most relevant. The cast or model of the arch being treated is duplicated for laboratory purposes. The ideal implant depth, as determined from the preoperative analysis, is transferred to the master cast or model. To maintain the desired level of the attached gingiva, it is generally accepted that the implant depth should be three millimeters apical to that level. The tissue thickness at the desired level of placement is determined using a ridge caliper with rubber depth stops.

The implant site on the cast or model is reduced to this level reflecting the future implant fixture level height. The thickness of the periodontium, on the facial and palatal/lingual aspect at this level, is now transferred to the master cast in the form of marking the cast site, or by reduction of the cast by probed caliper depth measurement. This in essence reduces the cast dimension in that site, taking care to follow the pre-existing topography of the model. The residual cast volume at the site should be an accurate reflection of the osseous bone volume available for implant placement at that level on the model. When there are no extremes in anatomic bone volume either by prominences or undercuts, this should also reflect the bone volume more apical to the crest of the implant. Measuring a minimum of two millimeters inward from the new facial dimension of the cast will be the determinant for the absolute facial position of the Implant Replica in the cast. Ideally, the Implant Replica should be positioned with an emergence two millimeters more palatal than the adjacent teeth to allow for an optimal emergence profile and final restoration. The angulation for insertion of the Implant Replica into the master cast is made by a paralleling of the incisal or cuspal inclination of the adjacent teeth after the reduction of the cast. The interproximal distance from the adjacent teeth or implants should be transferred to the cast as the final determinant of the implant position and size of fixture. The Implant Replica is then inserted into the cast after the site is prepared, using the same inclination. The author uses a drill press with an angulation guide to facilitate more accurate preparation of the cast, especially in cases where preoperative tomography has been acquired. The Implant Replica is then positioned and luted to the cast in the desired position. Care should be taken to place the Implant Replica with the proper rotational position or timing which may need to be duplicated during surgery if a restoration is prepared in advance. Creation of the surgical template now takes place using the Guided Cylinder with Pin and Guided Sleeve assembly which enables the precise reproduction of the Implant Replica's position at the time of surgery. The construction of the surgical template takes form with the use of an acrylic full-arch occlusal table that incorporates the Guide Sleeve. It is recommended that several inspection windows be created by removal of acrylic at a cusp or incisal edge directly on either side of the guide and in at least one posterior location on each side of the arch. At the time of surgery, the surgical template is seated on the occlusal surface of the surgical arch and the accuracy of fabrication can now be verified. A soft-tissue moulage reproducing the tissue volume and topography can be made on the working model, allowing the clinician to evaluate the results of the Implant Replica positioning with respect to the potential impact of fixture depth on the final gingival height and architecture. It also allows for the restorative team, in concert with the dental laboratory, to select the provisional and final restorative abutments in advance of the surgery and prior to the restorative phase. If provisionalization of the implant is planned, the Immediate Temporary Abutment is placed on the Implant Replica and the provisional restoration can be fabricated at this time. The position of the Implant Replica will now serve as the implant axis for construction of the provisional restoration, matching the topographical characteristics and contact position of the existing restoration to be duplicated. Alternatively, the final abutment may be selected in advance using this technique, and delivered at the time of implant placement using either a provisional restoration or the final restoration, depending upon the operator's preference and experience.

Application

Stabilization of the surgical template should be accomplished on each side of the arch whenever possible. The author uses a bite block on each side to reduce the chance of surgical guide movement at the time of surgery. The inspection windows are checked at this time and regularly throughout the procedure. The series of guided drills are used in sequence with their respective Guided Drill Guides to produce the desired osteotomy dimensions and depth.

The Implant Mount is used to deliver the implant in the predetermined position with a minimum insertion torque value of 35 Ncm. Note the rotational positioning of the implant is matched to the facial lobe of the Implant Replica in the model.

The Immediate Temporary Abutment is then placed and torque to 35 Ncm which also serves to verify primary stability of the implant. The Plastic Coping Immediate Temporary Abutment is placed on the abutment. The internal walls of the acrylic temporary crown are then relined with a flowable composite and the provisional seated to the ideal position and rotation on the abutment sleeve. The provisional is then light-cured, bonding it to the underlying Plastic Coping. The restoration is removed and any residual flashing is removed. An escape hole for temporary cement is created through the Plastic Coping, exiting the lingual fossa.

Temporary cementation the restoration with the patient in occlusion is completed. Articulating paper is used to check centric and all excursive movements to confirm, or adjust, so the provisional restoration is completely out of occlusion. The site is thoroughly cleansed to remove any residual debris from the soft tissue. An intrapoerative tomogram was taken before placement of the provisional to confirm the angulation of the implant was in keeping with the preoperative treatment plan. Strict postoperative instructions are given to the patient to avoid functional use of the provisional restoration during the first 6-12 weeks. After that period, the provisional restoration can be removed and the final restoration delivered.

CT-Guided Immediate Implant Placement with Full Arch Provisionalization in a Partially Dentate Patient.

Another recent advance in dental implants is CT Guide services for dentate patients. This procedure was developed by Dr. David A. Salmassy. The use of computed tomography (CT) technology for placement of dental implants has allowed the surgical and restorative team to idealize and optimize dental implant placement and the subsequent restorative prosthetic design. The clinical requirements of CT guided implant surgery have unfortunately been limited to the edentulous (without teeth) patient, whether fully missing teeth in the desired arch or missing teeth partially in the arch. Treatment planning software such as Nobel-Guide™ software technology has historically required the use of an acrylic processed imaging guide, with close adaptation to the soft tissue topography of the edentulous site, but it is limited to those sites that are edentulous. For the immediate extraction patient, the imaging guide has no soft tissue or ridge adaptation, based on the position of Nobel Biocare (Nobel Biocare presentation, Aug. 27, 2006, Slide 14). Nobel Biocare's disclaimer that there is no indication for the dentate patient or the immediate extraction patient resulted in a limitation of the use of the NobelGuide™ Software to only the fully or partially edentulous patients with radiographic imaging guides. This has been a shortcoming of their application.

NobelGuide™ Software is software that can be utilized for imaging and also to aid in the construction of surgical guides. This type of software will be referred to as "treatment planning" software.

In dental implant practices, it's easy to get mired in the details of case management, forgetting the time commitment we ask of our patients. But if treatment time can be consolidated, both the practice and the patient benefit. Reducing the time requirement from 6-10 visits to only 3 or 4 is a win-win objective—and one that promotes the patient's well-being and goodwill.

Recent developments have made it possible to do exactly that, while delivering successful and aesthetic full-arch restorations. The successful immediate loading of fixed, implant-supported full prostheses has been well documented. Dr. Paolo Maló who popularized the concept of full-arch fixed-prosthetic restoration predicated on four implants with angled implant placement. The results from his work offer great insight into optimizing patient treatment with a reduction of the number of implants.

Although traditional placements of 4 to 6 anterior implants have often resulted in long, biomechanically unfavorable posterior cantilevers, the All-on-4™ concept developed by Dr. Maló avoids this problem while using only four implants. Two are placed in the anterior, while two placed in tilted posterior positions are used in conjunction with special angle-correcting abutments. This strategy enables placement of significantly longer posterior implants, increasing the bone-to-implant contact, improving the force distribution, and improving occlusion.

The use of 3-dimensional computer-based technology now makes it possible to plan implant placements that can be restored optimally. Surgical Templates are then generated that enable the accurate placement of the implants using minimally invasive surgical techniques. When computer-guided planning is combined with the All-on-4™ concept, the benefits to the patient can be dramatic. Moreover, a recent study evaluating the integration of the All-on-4™ immediate function concept with computer guided implant placement (NobelGuide™, Nobel Biocare AB, Goteborg, Sweden) has shown that this modality can be predictable with a high implant-survival rate.

The following case illustrates the use of computer guided technology to implement the All-on-4™ concept for a partially edentulous patient requiring extraction of his remaining anterior dentition.

The patient was a 63-year-old male with a 12-year history of wearing an upper partial denture. When his third such prosthesis broke, he sought a fixed restorative dental solution. A panoramic radiograph revealed compromised bone height and volume surrounding the remaining maxillary teeth, with the sinus floor favorably positioned just above the roots of the posterior teeth.

It was explained to the patient that if three implants were placed on each side, the insufficient bone height and volume would not allow for use of long implants in the posterior, increasing the chance of implant failure. The patient instead indicated a desire for immediate reconstruction of four implants, with the placement of those implants to be planned using the NobelGuide™ technology.

The patient's existing partial denture was duplicated in clear acrylic, and 8 radiopaque gutta percha markers approximately 1.5 mm in diameter and 1 mm deep were added to the duplicate denture. The markers were positioned per the published protocol. The duplicate denture is now ready to serve as a Radiographic Guide. At the same time, a bite registration was fabricated to stabilize the Radiographic Guide against the soft tissue and adjacent teeth in the maxillary arch and to open the bite vertically for the computed tomography (CT) scan.

An Imaging Sciences i-CAT CT scan was generated with the patient wearing the Radiographic Guide with the bite registration. The radiographic guide was then scanned alone, and the data from both scans were loaded into the three-dimensional Procera® Software Planning program (Nobel Biocare) and superimposed upon each other, using the radiopaque markers as reference points.

Having the 3-D image of the bone in relation to the position of the denture greatly facilitates planning the position and angulation of the implants and anchor pins. It was decided to place four NobelReplace™ Tapered Groovy implants in the positions of teeth 4, 7, 10, and 13. All four implants were 4.3 mm in diameter and 16 mm long, (32218) with the two posterior implants to be intentionally angled distally to avoid the anterior wall of the maxillary sinus. Two 300 angulated multi-unit abutments (33409, NobelGuide™, Nobel Biocare) were then used on the distal implants to allow for easy prosthetic screw access and prosthesis placement while creating a parallel path of insertion relative to the anterior implants. These abutments are non-engaging, a necessity because the NobelGuide™ system primarily controls vertical and horizontal implant positioning, but not rotational positioning.

The use of an acrylic resin jig is necessary between the anterior straight multi-unit abutments and the posterior angulated abutments for proper abutment orientation transfer from extra-oral preparation to intra-oral setting. The all-resin prosthesis can be pre-fabricated using temporary copings. However, one or both distal temporary copings(s) is/are not included in the prosthesis and will usually be picked up and incorporated to the prosthesis intra-orally at the time of prosthesis placement.

If the All-on-4™ concept is being carried out using distal implants that are angulated less than 30°, the use of angulated multi-unit abutments is not necessary. Instead, non-angulated vertically adjustable guided abutments can be employed. Using such guided abutments eliminates the need for the time-consuming temporary coping pick-up process and may allow for placement of a definitive prosthesis at the time of surgery.

In this case, three Guided Anchor Pins were planned for placement with one in the midline and the other two in between the two implants on each side, perpendicular to the labial cortical plate. The data were then sent digitally to Nobel Biocare for fabrication of a stereolithographic Surgical Template containing the guide sleeves for the anchor pins and the implant surgical drill guide inserts. The Surgical Templates are made of a light-sensitive resin. Because this is susceptible to moisture and ultraviolet light, the resin guide must be stored in a dark, dry location such as a UV-protective plastic bag in conjunction with a moisture absorber when not in use.

The Surgical Template was used to create a working model housing the implant replicas and a soft-tissue moulage. This model was then retrofitted to the opposing arch, using the same Radiographic Index (bite registration) and Radiographic Guide that were worn during the CT scan. The provisional restoration was then created with the appropriate laboratory components. The final step was the formation of the Surgical Template index, which is a bite registration between the Surgical Template, attached to the implant replicas and the opposing arch. This is used for definitive positioning and stabilization of the Surgical Template prior to implant placement.

Immediately before surgery, the Surgical Template was soaked in disinfecting solution for ten minutes, rinsed with sterile water, and air-dried. The use of any heat must be avoided to prevent deformation of the template.

After administration of local anesthesia, the remaining maxillary teeth were removed, except for the two molars. The Surgical Template was placed in position, using the Surgical Index and the opposing arch, with the two molars helping to retain and maintain the position of the template. A 1.5 mm twist drill was used to place the Guided Anchor Pins and thus secure the Surgical Template to the maxilla. The two anterior implants were placed, followed by the distal two. The Surgical Template was removed, and the remaining molar teeth were extracted. Tissue healing abutments were placed to prevent any collapse of the soft tissue into the implants collar. The patient was then transferred to the office of the restorative doctor for placement of the temporary prosthesis. Upon follow-up the next day, the patient presented with the provisional restoration comfortably in place. No swelling was evident.

With the prosthesis in position, the implant prosthetic abutments is attached and secured to the prosthesis. Note that the implant positions are inside the existing teeth, important for both the provisional and final restorations. Also important is the open palate in the provisional prosthesis. Patients who have never had the palate covered might otherwise experience a gag reflex. The open palate would be maintained in the final restoration as well.

After three months, the patient returned for removal of the temporary prosthesis. Torque testing of all four implants confirmed that the initial primary stability of 35 Ncm achieved at the time of placement had been maintained. The patient was also satisfied with the appearance and function of the provisional restoration.

The restorative doctor was notified that the patient was ready to proceed clinically with the fabrication and placement of the final prosthesis. The final prosthesis was delivered two weeks later, only fourteen weeks after the single surgical procedure, and sixteen weeks after the patient's initial consultation.

When using the All-on-4™ approach, proper case selection is imperative. Good systemic health and sufficient bone volume are essential, along with an understanding by the patient of the need to maintain a soft, blenderized, non-chew diet for the initial 4 to 6 weeks after implant placement.

When combined with NobelGuide™, the All-on-4™ approach enables patients to experience far less pain and swelling than possible with traditional surgical protocols where significant tissue flaps are required for access to the osteotomy sites. Final restoration can be accomplished anywhere from six to eight months sooner than the typical three-stage surgical approach for similar cases. Implant positioning can be carried out with a precision never before possible.

Patients are now doing their homework on implant dentistry and are learning about the technological advances that not only change the way their care can be delivered, but the timeliness of this approach to treatment. The corresponding professional impact is higher patient understanding prior to treatment and higher case acceptance for the surgical and restorative practitioner as well.

The practice-management mantra that has fueled our practice success is simple: patients don't come to us for surgery. They come because they want to replace their failing or missing teeth. Approaching that end by focusing on the restorative objectives first and planning the surgery to accomplish those objectives has enabled us to consistently meet our patients' objective. The restorative goal is to provide our patients with replacement teeth that look beautiful and function well. The surgical goal is to deliver the foundation for these teeth in a predictable, minimally invasive and time-sensitive modality. All things considered, patients gravitate toward the practitioners who are using technology to advance their particular case.

CT Guided Surgery in the Dentate Patient

CT Guided surgery in the dentate patient can be accomplished by the use of a radiographic guide if the manufacturer of the guide adheres to certain guidelines. The software can then be used to treat the dentate patient as well, as noted in the following steps:

Protocol

Step 1: Cast Configuration of the Dentate Patient

The model or cast of the patient and the site of the desired imaging must be modified in such a fashion so as to reduce undercuts in the dentate areas. The use of dental stone or plaster can facilitate this.

Step 2: Imaging Guide Design in the Dentate Patient

The model of the patient should be marked out so that there is sufficient overlap of radiographic guide to allow for guide insertion and guide removal from the patient. The radiographic markers placed in the imaging guide must be out of the axial plane of metallic restorations that would result in a scatter pattern on the CT scan, and would prevent the software from identifying the marker when interpreting the DICOM (Digital Image Communications in Medicine) imaging file in the software.

Step 3: Vacuum-Adapted Thermoplastic Radiographic Guide Construction.

The cast is modified to allow for air escape in the adaptation of the thermoplastic material at the time of construction. The excess material, beyond the markings on the cast can then be trimmed off and the guide reduced to the necessary volume of material that is required (2-3 mm) at the sites.

Step 4: Imaging of the Patient with the Radiographic Guide.

The NobelGuide™ protocol of imaging the patient both with the imaging guide and the radiographic guide alone is then completed.

Step 5: NobelGuide™ Software Surgical Planning

The NobelGuide™ software is then used to design the surgery, using the radiographic guide such that the alignment of the implants and there corresponding guide sleeves have at least one point of contact with the imaging guide wall s. The guide can then be accepted for conversion into a surgical guide by the software.

Hence, Treatment planning software such as Nobel-Guide™ software technology can be used for immediate extraction in dentate patients.

Although the present invention is illustrated below with regard to a few limited examples, it is understood that the present invention is applicable to any health care services situation where there are multiple professional functions and services are required for patient care. For example, one skilled the art will recognize that other embodiments are possible such as an embodiment where imaging is remotely located.

The dental terms used in this specification will be readily understood by one skilled in the art of dental implants. A reference for these dental terms is "International Congress of Oral Implantologists, Glossary of Implant Dentistry", Copyright 2004 by ICOL, Inc. This publication is incorporated by reference.

In another exemplary embodiment, a method for providing dental implant and restorative services to a patient having a dentate dental site comprises: generating a model of a patient's dentate dental site that is used to generate an imaging guide, the dentate dental site including one or more teeth to be extracted and replaced with an implant utilizing a computed tomography (CT) guided surgical guide; fabricating the CT guided surgical guide comprising the steps of: designing and fabricating an imaging guide from thermoplastic material; adjusting the imaging guide, the adjusting comprising the steps of: generating a modification of the model by reducing undercuts in the dentate dental site; marking the model to provide overlap in design of the imaging guide to provide imaging guide insertion and removal from the patient during CT guided imaging process; performing a first modification to the imaging guide by conforming the imaging guide to the modified model; performing a second modification to the imaging guide by extending or trimming the imaging guide to the markings; and installing radiopaque gutta percha markers into the imaging guide, wherein the gutta percha markers are placed out of an axial plane of any existing metallic restorations that result in a scatter pattern on CT image data which prevents surgical planning software from properly identifying radiographic gutta percha markers when interpreting a radiographic imaging file that is used in surgical treatment planning software.

The method also comprises generating first CT scan data of the patient wearing the imaging guide, the CT scan data including bite registration data; generating second CT scan data of the imaging guide alone; loading the first CT scan data and the second CT scan data into the treatment planning software and superimposing the first CT scan data and the second CT scan data using the radiopaque gutta percha markers as references points to generate a third set of image data, wherein the third set of image data renders an image of bone, teeth, and soft tissue in relation to a position of the imaging guide; and fabricating the CT guided surgical guide utilizing the third set of image data.

The method also comprises extracting the one or more teeth from the patient's dentate dental site; immediately performing an implant placement utilizing the CT guided surgical guide after extraction at the dentate dental site; and performing the recited steps of providing dental implant and restorative services to a patient having a dentate dental site within a single one-day appointment. The method further comprising generating diagnostic imaging of a patient's dental condition using a CT scanner. The third set of image data renders the image of bone, teeth and soft tissue that is a three dimensional image.

The method further comprises generating a dental implant and restorative treatment plan based on CT guided/assisted implant surgery services by: examining the patient by a restorative doctor; reviewing CT scanner imaging results by the restorative doctor and a surgeon; developing the dental implant and restorative treatment plan by the restorative doctor and the surgeon; discussing dental implant options with the patient comprising the dental implant and restorative treatment plan; and obtaining an approval of the dental implant and restorative treatment plan by the patient, wherein the dental implant and restorative services provided are co-located at one physical location.

The dental implant and restorative services further comprises, at one physical location: designing an implant prosthesis by a restorative doctor, and sending the design to a dental laboratory; manufacturing the implant prosthesis at the dental laboratory, wherein a surgeon monitors the dental laboratory; inspecting and approving the implant prosthesis by the restorative doctor; managing progress of a restoration process by a treatment coordinator; extracting teeth and modifying bone volume by the surgeon; placing dental implants in the patient; generating images of surgery of the patient at an imaging location; and reviewing and approving imaging results by the surgeon and restorative doctor; initiating final restoration process by the restorative doctor; and confirming that dental implant and restoration are successfully completed by the treatment coordinator.

The method further comprises utilizing one physical location for the services wherein the services provided are co-located at the one physical location; and providing to the patient at the one physical location, the services related to a treatment coordinator, a restorative doctor/prosthodontist, a surgeon, an imaging location, and a dental laboratory, wherein the dental implant and restorative treatment services are completed within a single one day appointment. The patient also has an edentulous dental site and the patient receives CT guided/assisted implant surgery services for both the dentate dental site and the edentulous dental site. The immediate implant placement with single tooth, partial, or full arch restoration is provided by CT guided/assisted implant surgery services.

What is claimed is:

1. A system for placement of one or more dental implants at dentate and edentulous sites comprising:
    one or more computers and one or more storage devices storing instructions which are operable, when executed by the one or more computers, to cause the one or more computers to perform operations comprising:
        importing a first scan data set and a second scan data set into a treatment planning software, wherein:

the first scan data set comprises a digital image of a patient's jaw representing hard and soft tissues of the patient's jaw including dentate and edentulous sites; and the second scan data set of the patient's jaw comprises a computed tomography (CT) digital image;

computationally combining the first scan data set and the second scan data set to produce a third data set of image data that renders a digital image of a bone, the dentate and edentulous sites, and soft tissue of the patient;

generating a treatment plan utilizing the third data set within the treatment planning software, wherein the treatment plan comprises an implant surgical plan; and generating a single surgical guide data set utilizing the third data set within the treatment planning software for fabrication of a single surgical guide for placement of one or more dental implants at the dentate and the edentulous sites; and a 3D printer, wherein the 3D printer receives the single surgical guide data set and fabricates the single surgical guide for placement of the one or more dental implants at the dentate and the edentulous sites.

2. The system according to claim 1, wherein an extraction of teeth for the dentate sites, a modification of the bone, and the placement of the one or more dental implants are performed at one physical facility.

3. The system according to claim 1, wherein:
the one or more computers perform operations comprising exporting the single surgical guide data set for the fabrication of the single surgical guide; and
the single surgical guide data set is generated at a first physical facility.

4. The system according to claim 3, wherein the single surgical guide is fabricated at the first physical facility based on the exported single surgical guide data set.

5. The system according to claim 1, wherein the single surgical guide data set comprises a three-dimensional file format.

6. The system according to claim 1, wherein the first scan data set comprises a modified cast of the patient's jaw representing the dentate and edentulous sites.

7. The system according to claim 1, wherein the first scan data set comprises the digital image of a physical model of the patient's jaw utilizing a CT scanner.

8. The system according to claim 1, wherein the first scan data set comprises the digital image of the patient's jaw utilizing a digital scanner.

9. A method for placement of one or more dental implants at dentate and edentulous sites comprising:
importing, via at least one processor, a first scan data set and a second scan data set into a treatment planning software, wherein:
the first scan data set comprises a digital image of a patient's jaw representing hard and soft tissues of the patient's jaw including the dentate and the edentulous sites; and
the second scan data set of the patient's jaw comprises a computed tomography (CT) digital image;
computationally combining the first scan data set and the second scan data set to produce a third data set of image data that renders a digital image of a bone, the dentate and edentulous sites and soft tissue of the patient;
generating a treatment plan utilizing the third data set within the treatment planning software, wherein the treatment plan comprises an implant surgical plan; and
generating a single surgical guide data set utilizing the third data set within the treatment planning software;
fabricating, via a 3D printer, a single surgical guide for placement of the one or more dental implants at the dentate and the edentulous sites.

10. The method according to claim 9, wherein extraction of teeth for the dentate sites, modification of the bone, and the placement of the one or more dental implants are performed at one physical facility.

11. The method according to claim 9, wherein:
the method further comprises exporting the single surgical guide data set for the fabrication of the single surgical guide; and
the single surgical guide data set is generated at a first physical facility.

12. The method according to claim 11, wherein the single surgical guide is fabricated at the first physical facility based on the exported single surgical guide data set.

13. The method according to claim 9, wherein the single surgical guide data set comprises a three-dimensional file format.

14. The method according to claim 9, wherein the first scan data set comprises a modified cast of the patient's jaw representing the dentate and edentulous sites.

15. The method according to claim 9, wherein the first scan data set comprises the digital image of a physical model of the patient's jaw utilizing a CT scanner.

16. The method according to claim 9, wherein the first scan data set comprising the digital image of the patient's jaw utilizing a digital scanner.

* * * * *